United States Patent [19]
Stewart et al.

[11] Patent Number: 5,693,039
[45] Date of Patent: *Dec. 2, 1997

[54] VENOUS RESERVOIR BAG ASSEMBLY

[75] Inventors: Rodger L. Stewart, Lafayette, Colo.;
John T. Buckley, Newark, Calif.;
William D. Dalke, Aurora, Colo.;
Barry D. Reed, Longmont, Colo.;
Joseph A. Scibona, Littleton, Colo.

[73] Assignee: Cobe Laboratories, Inc., Arvada, Colo.

[*] Notice: The term of this patent shall not extend beyond the expiration date of Pat. No. 5,352,218.

[21] Appl. No.: 190,309

[22] Filed: Feb. 2, 1994

Related U.S. Application Data

[63] Continuation of Ser. No. 725,126, Jul. 3, 1991, Pat. No. 5,352,218, which is a continuation-in-part of Ser. No. 538,903, Jun. 15, 1990, abandoned.

[51] Int. Cl.⁶ ........................................................ A61J 1/05
[52] U.S. Cl. ........................ 604/407; 604/403; 604/181; 604/408; 206/363; 222/65; 222/103
[58] Field of Search ........................... 604/407, 403, 604/181, 408, 404, 182, 4, 5, 151, 153, 317, 322, 131; 206/363; 222/65, 66, 103; 248/95

[56] References Cited

U.S. PATENT DOCUMENTS

| | | | |
|---|---|---|---|
| 50,085 | 9/1865 | Byrne . | |
| 3,366,276 | 1/1968 | Fridley | 222/51 |
| 3,565,292 | 2/1971 | Jinotti | 222/103 |
| 3,595,232 | 7/1971 | Leibinsohn | 128/214 |
| 3,625,401 | 12/1971 | Terry | 222/103 |
| 3,642,047 | 2/1972 | Waage | 150/8 |
| 3,734,351 | 5/1973 | Gaudin | 222/103 |
| 3,902,635 | 9/1975 | Jinotti | 222/103 |
| 3,907,504 | 9/1975 | Hammond et al. | 23/258.5 |
| 3,942,529 | 3/1976 | Waage | 128/272 |
| 3,992,706 | 11/1976 | Tunney et al. | 340/239 R |
| 4,004,590 | 1/1977 | Muriot | 128/276 |
| 4,019,656 | 4/1977 | Spears | 222/103 |
| 4,019,707 | 4/1977 | Quinn et al. | 248/95 |
| 4,058,363 | 11/1977 | Silbert | 604/403 X |
| 4,085,866 | 4/1978 | Fekl | 222/158 |
| 4,157,771 | 6/1979 | Smith | 222/103 |
| 4,187,845 | 2/1980 | Dror | 128/205.13 |
| 4,284,209 | 8/1981 | Barbour, Jr. | 222/1 |
| 4,316,576 | 2/1982 | Cullis et al. | 233/26 |
| 4,378,014 | 3/1983 | Elkow | 128/214 E |
| 4,393,880 | 7/1983 | Taylor | 604/322 X |
| 4,447,939 | 5/1984 | Taylor | 604/322 X |
| 4,451,259 | 5/1984 | Geissler et al. | 604/408 |
| 4,496,354 | 1/1985 | Steer et al. | 604/322 |
| 4,500,311 | 2/1985 | Redmon et al. | 604/326 |
| 4,557,728 | 12/1985 | Sealfon et al. | 604/134 |
| 4,626,243 | 12/1986 | Singh et al. | 604/141 |
| 4,642,089 | 2/1987 | Zupkas et al. | 604/4 |
| 4,650,452 | 3/1987 | Jensen | 604/408 X |
| 4,976,851 | 12/1990 | Tanokura et al. | 210/86 |
| 4,991,743 | 2/1991 | Walker | 222/103 |
| 5,049,146 | 9/1991 | Bringham et al. | 604/4 |
| 5,061,236 | 10/1991 | Sutherland et al. | 604/4 |
| 5,061,451 | 10/1991 | Ganshirt et al. | 472/101 |
| 5,078,677 | 1/1992 | Genetelia et al. | 604/317 X |
| 5,238,582 | 8/1993 | Hori et al. | 604/403 |

FOREIGN PATENT DOCUMENTS

| | | |
|---|---|---|
| 0 093 982 A1 | 5/1982 | European Pat. Off. . |
| 0 198 869 B1 | 12/1988 | European Pat. Off. . |
| 1408360 | 7/1964 | France . |
| 7708421 | 2/1978 | Netherlands . |
| WO 94/08645 | 4/1994 | WIPO . |

OTHER PUBLICATIONS

Deknatel, Pleue–Evvc Auto Transfusion System, 1986.

*Primary Examiner*—Danton D. DeMille
*Attorney, Agent, or Firm*—Holme Roberts & Owen

[57] ABSTRACT

A venous reservoir bag subassembly which is adapted to cooperate with a mounting assembly having a bracket frame and a front plate reproducibly relatively movable to enable constant accurate blood volume readout, a cooperating mechanism between the subassembly and the mounting assembly to provide against unduly low blood volume, and an angled conduit cooperating with the bag and recesses in the subassembly and assembly to provide further failsafe against passage of the undesirable gas.

19 Claims, 4 Drawing Sheets

VENOUS RESERVOIR BAG ASSEMBLY

RELATED APPLICATIONS

This application is a continuation of U.S. patent application Ser. No. 07/725,126, filed Jul. 3, 1991, now U.S. Pat. No. 5,352,218 by John T. Buckley, William D. Dalke, Barry D. Reed, Joseph A. Scibona, and Rodger L. Stewart entitled "VENOUS RESERVOIR BAG ASSEMBLY", which is in turn a continuation-in-part of U.S. patent application Ser. No. 07/538,903, filed Jun. 15, 1990, now abandoned by John T. Buckley, William D. Dalke, Barry D. Reed, Joseph A. Scibona, and Rodger L. Stewart entitled "VENOUS RESERVOIR BAG ASSEMBLY, "both of which are hereby incorporated by reference.

FIELD OF THE INVENTION

This invention relates to extracorporeal body fluid reservoirs used to store body fluids during surgical procedures, and more particularly to venous reservoir closed bag assemblies useful for extracorporeal storing of blood from a patient (e.g., in cardiopulmonary bypass procedures).

BACKGROUND OF THE INVENTION

In many surgical procedures blood is removed from a patient and passed through an extracorporeal circuit. For example, during open heart surgery blood may be directed into an extracorporeal circuit for oxygenation and filtration. The blood diverted from the patient's body is stored temporarily in at least one extracorporeal reservoir, typically called a venous reservoir.

There are two general types of known venous reservoirs: open reservoirs and closed reservoirs. Open reservoirs typically comprise a rigid shell into which blood is directed during surgery and accumulates from the bottom up. The reservoir may include a calibrated scale to allow an operator, or perfusionist, to readily determine the volume content of blood in the reservoir. However, open venous reservoir systems currently employed do not provide for the automatic detection of low blood levels in a reservoir.

In open reservoirs an air to blood interface typically exists along the top surface of the blood in the reservoir. As such, gas bubbles within the blood can migrate upward in the reservoir and escape. However, prolonged exposure of the blood near the surface may damage components of the blood.

Closed reservoirs typically are closed bags formed from plastic or other non-porous material which deforms under pressure. These bags may be suspended from a stand located near the patient. Blood is typically directed into the bottom of the bag through an inlet tube and exits the bag through an outlet tube located near the bottom of the bag. Because the bag deforms irregularly under pressure, closed reservoirs are not easily calibrated to reflect the volume of blood contained therein. Further, closed venous reservoir systems currently employed do not accommodate reliable low level blood detection.

Closed reservoirs typically have no blood to air interface as is common with open reservoirs. Therefore, closed reservoirs largely avoid blood damage caused by prolonged exposure of blood to air. However, gas bubbles may become entrapped within the contained blood because they cannot migrate upward to a blood to air interface. To alleviate this problem, reservoirs have been designed to include screen filters which remove gas bubbles from the blood. The gas bubbles may, for example, be vented from the bag through a vent located near the top of the bag.

SUMMARY OF THE INVENTION

Objects of the present invention are to provide a venous reservoir assembly wherein the receipt and dispensation of body fluid within a flexible reservoir is effected in a manner that allows for reliable volume determination, low level detection, gas bubble removal, and the realization of related advantages.

To meet the aforementioned objectives, we have mounted a flexible venous reservoir bag on a rigid plate to provide a closed bag and bag plate subassembly. This subassembly is desirably releasably latchable into a support assembly having a back support portion ("bracket frame") and a front portion ("front plate"), the portions being relatively movable in a constant spaced relationship to predeterminedly vary the instantaneous thickness (and thus volume) of the bag in a constant manner.

There is provided a closed bag system which is easy to use, with easy air handling and simplified accurate contents volume resolution.

DETAILED DESCRIPTION

Figure 1:
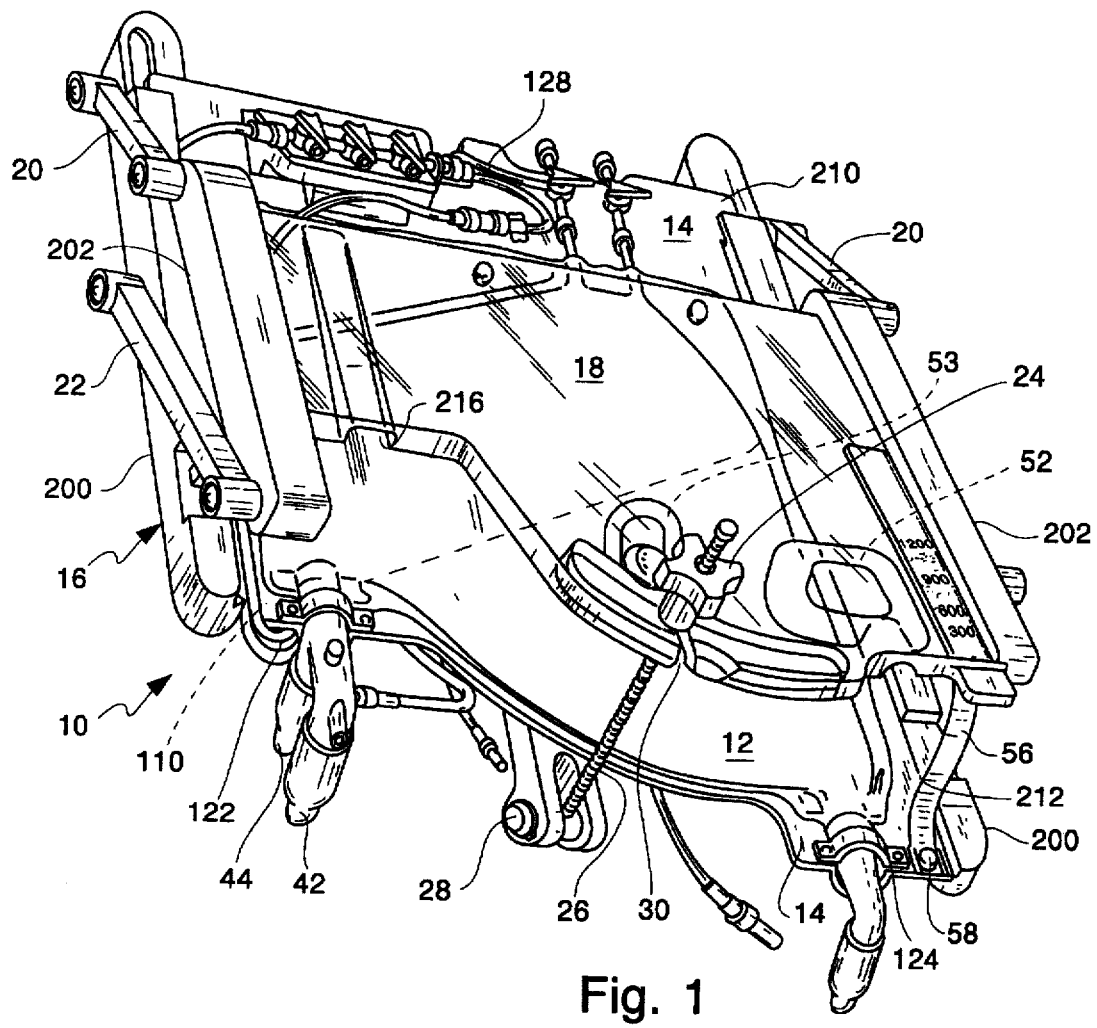
FIG. 1 is a perspective view of one embodiment of the disclosed invention showing the front portion adjacent the back portion and the volume-limiting nut stop in one position.

Referring now to FIG. 1, there is shown, in the embodiment indicated generally at 10, a subassembly comprising a closed flexible bag 12 (e.g. having a 1200 ml. capacity) and bag plate 14 seated in a support assembly between its bracket frame 16 and its front, or upper, plate 18.

Figure 3:
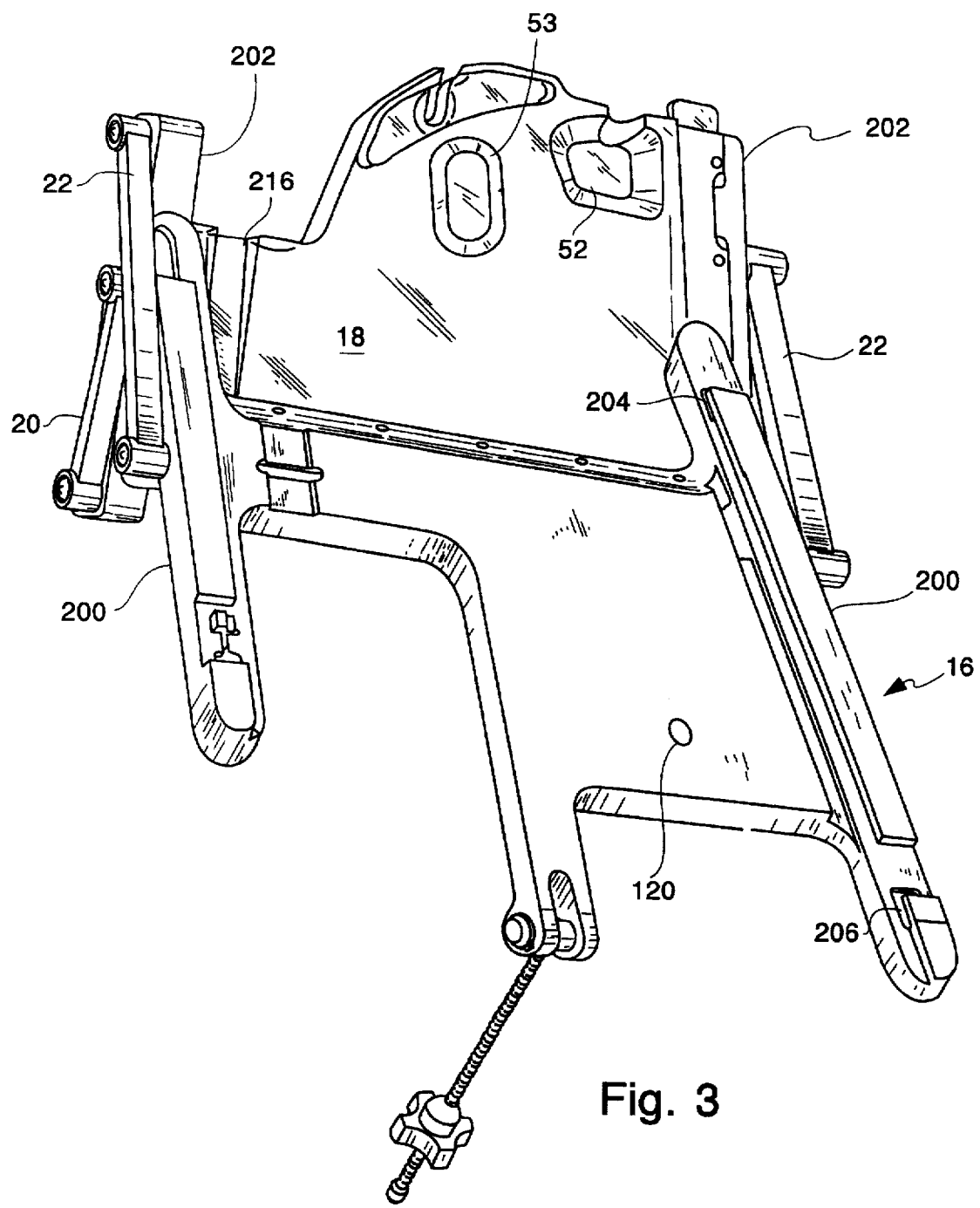
FIG. 3 is a perspective view of the support assembly of the embodiment with the bag and plate subassembly removed.
Figure 4:
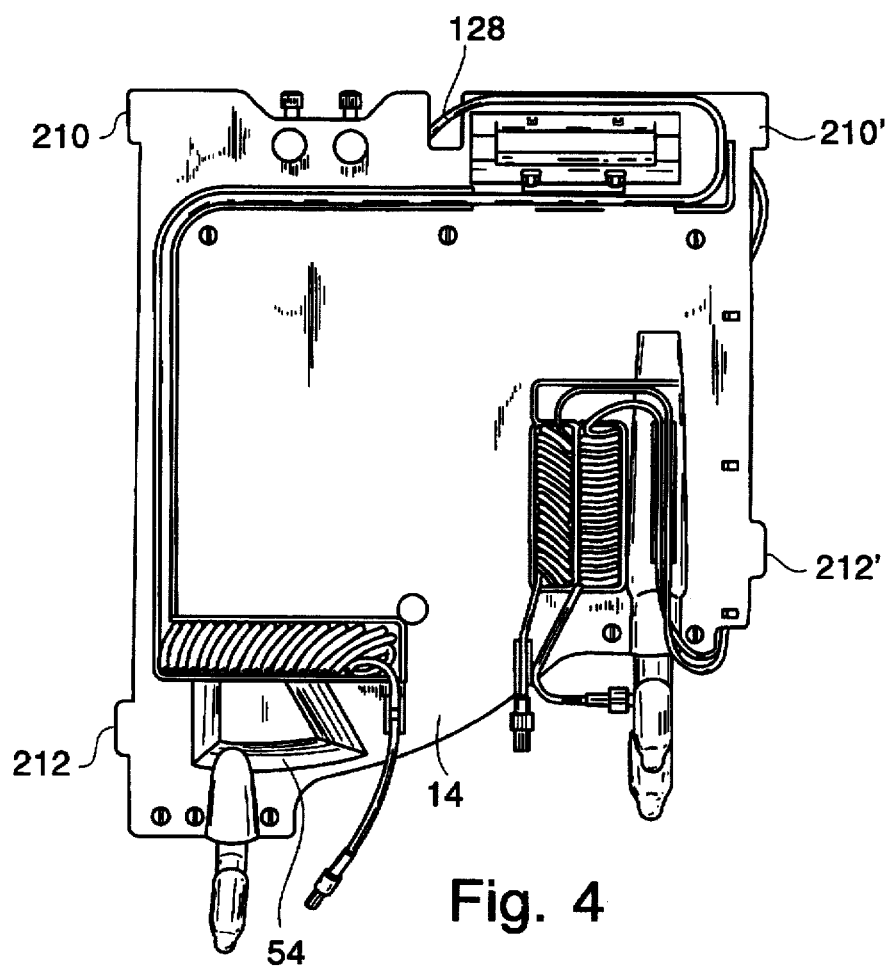
FIG. 4 is a rear elevation view of the bag plate of the embodiment.

As best shown in FIG. 3, bracket frame 16 of the illustrated embodiment is a substantially planar structure having side edges 200. Similarly, upper plate 18 is substantially planar and is secured to side edges 202. Bracket frame 16 and upper plate 18 are interconnected by two pairs of pivotal arms 20, 22 along side edges 200 and 202. Bracket frame 16 is dimensioned to receive bag plate 14 and includes slots (e.g. 204, 206 as best shown in FIG. 3) for receiving tabs (e.g. 210, 210', 212, 212' as best shown in FIG. 4) on bag plate 14 to retain bag plate 14 in a fixed position with respect to bracket frame 16.

Figure 2:
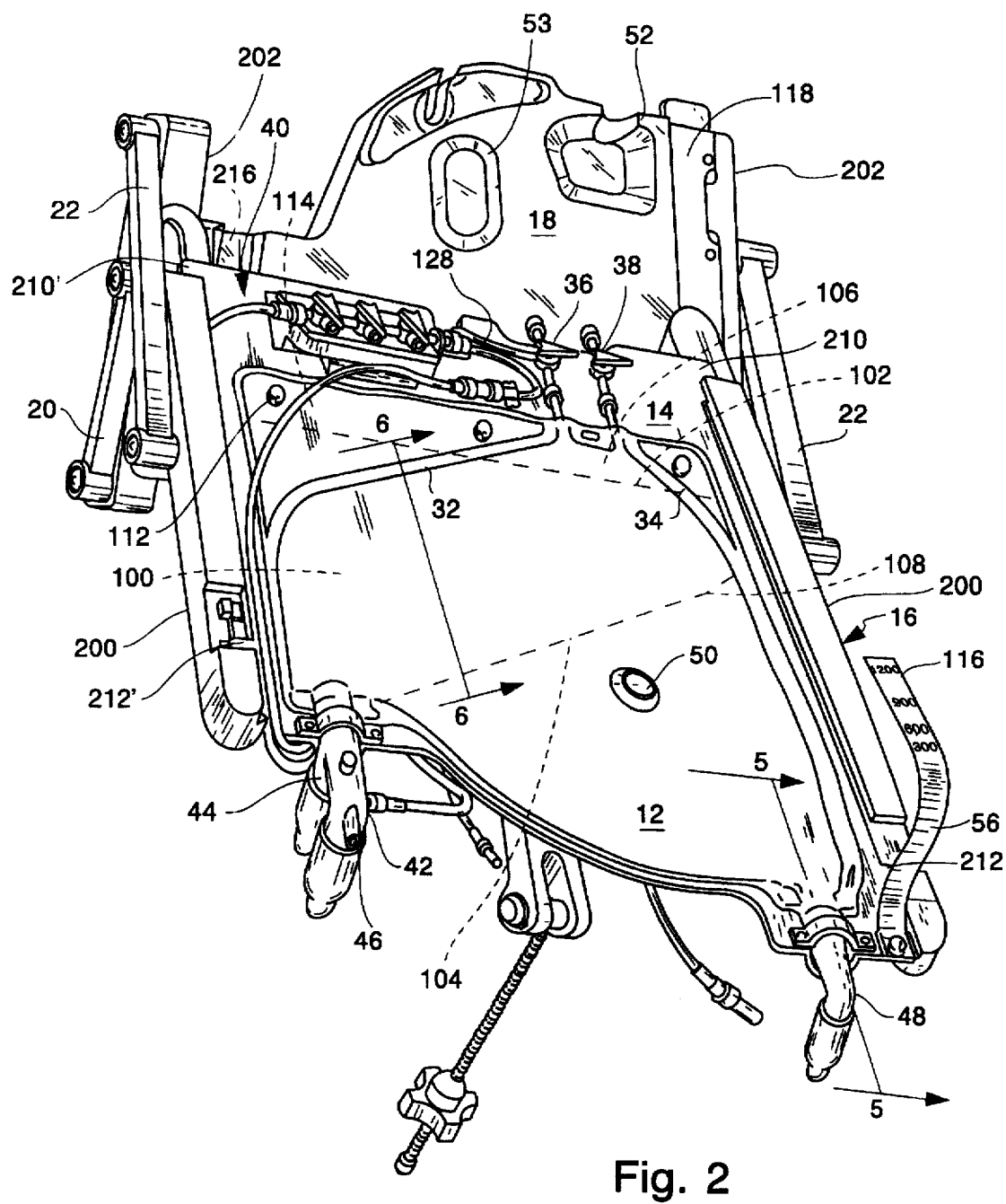
FIG. 2 is a perspective view of said embodiment showing the front portion moved away from the back portion.

Upper plate 18 is of a predetermined weight (e.g. approximately two pounds) and in the illustrated embodiment is connected with bracket frame (back plate) 16 by a pair of shorter arms 20 and a pair of longer arms 22. Each arm 20 and 22 is pivotally secured toward its back end to bracket frame 16 and toward its front end to front plate 18, in a relationship such that at one travel extremity, as shown in FIG. 1, the plates 16 and 18 are nearly parallel, while at the other travel extremity, as shown in FIG. 2, plates 16 and 18 are widely separated. At the first mentioned travel extremity, plates 16 and 18 are spaced to permit a predetermined volume (e.g. about 200 ml.) of blood to enter before the volume of blood begins to move front plate 18.

As best illustrated in FIGS. 2 and 3, the upper plate 18 includes a substantially flat lower surface having a first recess 52 and a second recess 216. In operation, the lower surface of plate 18 contacts the upper surface of bag 12. As the bag 12 fills with blood, pressure from the blood forces upper plate 18 away from lower plate 14 while the substantially parallel relationship therebetween is maintained. The flat lower surface of plate 18 causes the upper surface of bag 12 to remain substantially flat as the bag fills with blood.

The maximum distance between plates 16 and 18, and thus the maximum volume of bag 12, can be set by means of nut 24, which is threadedly carried by member 26 for uninterrupted continuously variable distance settings therealong, the member 26 being mounted for pivotal movement about pivot 28 carried by bracket frame 16, and engageable in slot 30 of front plate 18 to act as a stop therefor.

The bracket frame 16 is mounted (on pole means not shown) to support the bag and bag plate at an angle (e.g. 45°, or even more preferred, 55°) to the horizontal, the end of bag plate 14 at outlet 48, alongside the bottom of bag 12, being the lower end thereof.

Figure 5:
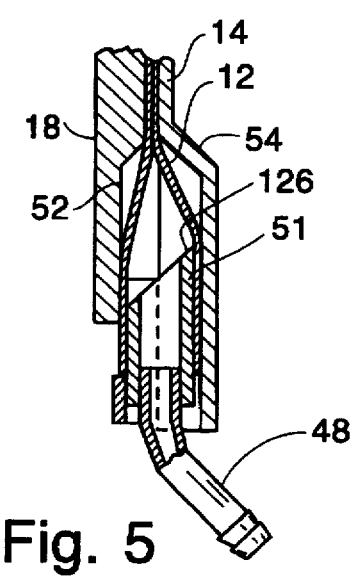
FIG. 5 is a sectional view taken at 5—5 of FIG. 2.
Figure 6:
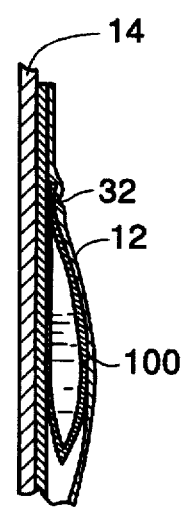
FIG. 6 is a sectional view taken at 6—6 of FIG. 2.

Bag plate 14 carries bag 12 as well as the outlets 36, 38, and the blood gas sample system 40. As best illustrated in FIGS. 4 and 5, bag plate 14 also includes recess 54 positioned adjacent to outlet tube 51. Recesses 52 and 54 cooperate to form a chamber which surrounds outlet tube 51 when front plate 18 and bag plate 14 are substantially adjacent.

Bag 12 is a flat bag formed of two layers of flexible vinyl sheet 114 RF welded around the periphery as at 32, 34. Bag 12 includes an inlet tube 110 and an outlet tube 51 disposed to allow the flow of blood into and out of reservoir 12, respectively. A woven polyester fabric (105μ apertures) double layer element 100 disposed between the vinyl layers aids in removing gas. This fabric element is secured in the above-mentioned RF weld above which it extends to the pair of edges 102, and is folded along edge 104. Disposing element 100 in this manner requires blood entering the reservoir through inlet tube 110 to flow through element 100 before exiting the reservoir through outlet tube 51. Gas bubbles removed by screen element 100 may be vented from the bag through gas outlets 36 and 38.

There are two bypass regions around the screen within the bag. One is the area 106 at the very top of the screen in the region of the vent lines to outlets 36, 38. Heat seal 32 does not extend through fabric layers 100 here. This bypass 106 is to facilitate removal of air from both sides of the screen. The other screen bypass 108 is located at the right-most part of the screen, farthest away from the venous inlet, a triangular portion of the double thickness of which is cut away. This is a safety bypass to minimize the possibility of pushing air through the screen in the extreme condition of running at very low reservoir volumes, and having a large amount of air collected in the screen without venting through the top of the bag. It also provides a bypass around the screen in the event the screen should become occluded.

Bag 12 includes as portions of it venous inlet 42, cardiotomy inlet 44, temperature probe 46, outlet 48, vent line 128 and magnet 50. Inlet 110, into which inlets 42 and 44 feed, is secured between the two layers of fabric element 100 within bag 12. Inlet tube 110 and outlet tube 51 are secured for immovability and thus strain relief with prevention of bag twisting in use by respectively clamps 122 and 124 secured to bag plate 14. The rigid bag plate 14 is of white plastic for contrast with blood level during use.

Insurance against drawing blood down too far with possible air entrapment is provided by the combination of magnet 50, mounted on the outer surface of bag 12 toward front plate 18, and a normally open reed switch sensor, carried by bracket frame 16 in hole 120 just below magnet 50 (e.g. protruding 0.100 inches above the surface of bracket frame 16) toward bag 12. When the volume of blood in bag 12 drops to a sufficiently low level, magnet 50 triggers the reed switch sensor to terminate operation. Front plate 18 includes recess 53 for receiving magnet 50.

A second shut off system is illustrated in FIG. 5. As discussed above, recess 52 in upper plate 18 and recess 54 in lower plate 14 form a chamber surrounding outlet tube 51, which is integrally attached to the walls of bag 12.

The outlet connector 48 is inserted into outlet tube 51 with an upper surface 126 at an angle (e.g. 45°) to the direction of blood flow and generally to the wall of bag 12. As illustrated in FIG. 5, as reservoir 12 empties upper plate 18 and lower plate 14 are substantially adjacent to one another and the remaining blood is collected in the chamber defined by recesses 52 and 54. As this chamber empties, the upper wall of reservoir 12 collapses over angled surface 126 of outlet tube 51, thereby restricting air flow through tube 51. This provides positive shutoff when the reservoir is emptied of fluid, the bag top surface moving appropriately against the angled surface.

Pockets 52 and 54 keep the walls of bag 12 away from outlet tube 51 to prevent possible premature shutoff of blood flow.

Volume readout is provided by virtue of flexible tape 56, which bears indicia 116 as shown in the drawings, has its lower extremity 58 anchored in bag plate 14, and has its upper portions moving in a slot 118 in upper plate 18. As noted above, upper plate 18 moves up and down within its predetermined range of motion in response to changes in volume of blood in reservoir 12. Flexible tape 56 is calibrated to reflect the volume of reservoir 12 as a function of the distance between upper plate 18 and lower plate 14.

Operation

In operation, a flexible reservoir bag 12 is secured to the lower plate 14 using connectors 112 and clamps 122 and 124. The lower plate 14 is then secured to the lower bracket structure 200 by sliding tabs (e.g., 210 and 212) into complimentary slats (e.g., 204 and 206). The assembly 10 is then disposed at an angle with respect to the horizontal such that gas vents 36, 38 are disposed vertically higher than inlet tube 110 and outlet tube 51.

As blood is introduced through inlet 110, it rises first in a direction generally parallel with the surface of bag plate 14, which is in turn parallel with bracket frame 16. After a predetermined amount of blood (e.g., 200 ml.) has entered the bag 12 and bag 12 is contacting bag plate 14 and front plate 18, further filling requires and results in movement of front plate 18, which in effect causes weighted front plate 18 to "float" on bag 12; during this stage, blood reservoir filling is in a direction basically perpendicular to the surface of bag plate 14. This double direction two-step approach to required blood reservoir filling provides consistent flow dynamics and air handling characteristics at all operating range blood levels. Also, reservoir fluid level is maintained in communication with vents 36, 38 throughout, and bag massage (with possible consequent release downstream of gas microemboli) is minimized. This filling action, plus the contrasting white plastic of bag plate 14, gives excellent low-volume (below 200 mL.) resolution.

The two bypasses and the angled outlet tube inlet surface contribute to this result.

Actually, the magnet 50 and sensor 60 ordinarily provide a predetermined lower limit on bag volume by triggering or otherwise providing appropriate signal means when they reach a predetermined distance apart. The angled surface 126, which cooperates with the adjacent bag wall to provide a complete cutoff without residual edge passages as when tubing is compressed between two flat surfaces, provides a secondary fail-safe in the event that the magnet and sensor somehow fail to do their job.

What is claimed is:

1. A body fluid reservoir assembly comprising:
a flexible reservoir for containing a body fluid;
a first lateral member positioned below said flexible reservoir;
a second lateral member positioned above said flexible reservoir, wherein one of said first and second lateral members includes a removable plate for releasably receiving said flexible reservoir, and said other of said first and second lateral members is selectively positionable to permit removal and placement of said plate; and
an interconnecting subassembly for interconnecting said first lateral member and said second lateral member, said interconnecting subassembly including a plurality of pivotal interconnecting members, at least one of said pivotal interconnecting members being disposed adjacent to a side edge of each of said first and second lateral members, and wherein said second lateral member has a predetermined weight, said flexible reservoir substantially entirely supports said weight of said second lateral member, and only said weight of said second lateral member to substantially entirely defines a predetermined distribution of said body fluid within said flexible reservoir during use.

2. The assembly of claim 1, wherein said interconnecting subassembly maintains a predetermined relative, spaced relationship between said first and second members during use, and wherein the distance between said first and second lateral members varies during use in direct response to the volume contents of said flexible reservoir.

3. The assembly of claim 2, further comprising:
means for flowing said body fluid into said flexible reservoir during use.

4. The assembly of claim 4, further comprising:
means for removing said body fluid from said flexible reservoir during use.

5. The assembly of claim 1 wherein said first member includes a first substantially planar plate, said second member includes a second substantially planar plate; and
wherein said first and second plates are maintained in a substantially parallel relationship during use.

6. The assembly of claim 1, said flexible reservoir comprising:
a bladder having at least one body fluid access means passing through an outer wall and disposed to allow the flow of body fluid therethrough during said use.

7. The assembly of claim 6, said body fluid access means comprising:
a body fluid inlet to allow body fluids to pass into said reservoir; and
a body fluid outlet to allow body fluids to pass out of said reservoir, wherein said body fluid inlet is disposed higher than said body fluid outlet during use to provide for gravity flow of said body fluid through said reservoir.

8. The assembly of claim 7, said flexible reservoir further comprising:
filtering means for filtering gas bubbles from said body fluid passing through said flexible reservoir, said filtering means being disposed between said body fluid inlet and said body fluid outlet.

9. The assembly of claim 8, said filtering means comprising:
a flexible mesh screen integrally interconnected with said bladder.

10. The assembly of claim 8, further comprising:
a bypass defining a flow path from said body fluid inlet, around said filtering means, to said body fluid outlet, wherein said bypass is disposed higher than both said body fluid inlet and body fluid outlet during use.

11. The assembly of claim 1, said flexible reservoir further comprising:
at least one gas outlet passing through an outer wall and disposed to remove gas bubbles from said body fluid.

12. The assembly of claim 11, further comprising:
a gas sampling means interconnected to said gas outlet for sampling said gas bubbles removed from said flexible reservoir during use.

13. The assembly of claim 1, said interconnecting subassembly further comprising:
means for establishing a predetermined maximum volume content of said flexible reservoir.

14. The assembly of claim 13, said means for establishing comprising:
a post interconnected at one end to said first lateral member and slidably interconnected at another end to said second lateral member; and
a stop member interconnected to said post to limit movement of said second lateral member during use.

15. The assembly of claim 1, further comprising:
an indicating means for indicating the volume contents of said flexible reservoir, said indicating means contacting one of said first and second lateral members at a first end, slidably contacting the other of said first and second lateral members at a second end, and being calibrated to indicate the volume contents of said flexible reservoir as a function of the distance between said first and second lateral members.

16. A body fluid reservoir assembly comprising:
a flexible reservoir for containing a body fluid;
a first lateral member positioned below said flexible reservoir;
a second lateral member positioned above said flexible reservoir;
means for interconnecting said first lateral member and second lateral member in a predetermined relationship that varies in a predetermined manner in response to the volume contents of said flexible reservoir; and
sensing means for sensing a predetermined relative position of said first and second lateral members and automatically generating a signal in response to said predetermined relative position, wherein said sensing means comprises:
a magnet attached to a first surface of said flexible reservoir; and
a switch, responsive to said magnet, disposed adjacent to a second surface of said flexible reservoir.

17. A body fluid reservoir assembly comprising:
a laterally positioned flexible reservoir having an internal containment space for containing a body fluid, said reservoir having a flexible top layer and a bottom layer opposing said top layer, and at least one outlet tube passing through an outer wall for dispensation of said body fluid from said internal containment space, said outlet tube having an inner end laterally projecting inward into said internal containment space of said reservoir, wherein the inner end of said outlet tube is angled to present an upward facing outlet;

a first lateral member contacting a bottom surface of said bottom layer of said laterally positioned flexible reservoir;

said top flexible layer and said inwardly projecting, angled inner end of said outlet tube being positioned wherein a bottom surface of said flexible top layer is free to automatically collapse to contact said upward facing outlet and thereby block the inner end of said outlet tube during dispensation of said body fluid from said flexible reservoir at a predetermined volume of body fluid within said internal containment space of the flexible reservoir.

18. The body fluid reservoir assembly of claim 17, further comprising:

a first recess defined in said first lateral member and disposed to receive a portion of said fluid reservoir containing said outlet tube during use.

19. The body fluid reservoir assembly of claim 17, further comprising:

a first recess defined in said first lateral member;

a second lateral member contacting a top surface of said top layer of said flexible reservoir and having a second recess, said first and second recesses defining a cavity within which a portion of said fluid reservoir containing said outlet tube is positioned during use.

* * * * *